United States Patent
Zhang et al.

(10) Patent No.: US 8,979,760 B2
(45) Date of Patent: *Mar. 17, 2015

(54) METHOD AND APPARATUS FOR AUTOMATIC OPTIMIZATION OF DOPPLER IMAGING PARAMETERS

(75) Inventors: Yu Zhang, Shenzhen (CN); Guanxi Zhang, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 309 days.

This patent is subject to a terminal disclaimer.

(21) Appl. No.: 13/428,364

(22) Filed: Mar. 23, 2012

(65) Prior Publication Data

US 2012/0179047 A1  Jul. 12, 2012

Related U.S. Application Data

(63) Continuation of application No. 12/198,569, filed on Aug. 26, 2008, now Pat. No. 8,142,361.

(30) Foreign Application Priority Data

Aug. 28, 2007  (CN) .......................... 2007 1 0148460

(51) Int. Cl.
*A61B 8/06* (2006.01)
*G01S 15/89* (2006.01)
*G01S 7/52* (2006.01)

(52) U.S. Cl.
CPC ............... *A61B 8/06* (2013.01); *G01S 15/8986* (2013.01); *G01S 7/5205* (2013.01); *G01S 15/8981* (2013.01)
USPC .......................................... 600/455; 600/453

(58) Field of Classification Search
CPC ..... A61B 8/06; G01S 15/8981; G01S 15/8986; G01S 7/5205
See application file for complete search history.

(56) References Cited

U.S. PATENT DOCUMENTS 6,176,830 B1 *  1/2001  Freiburger .................... 600/453
6,447,455 B2    9/2002  Bang et al.
(Continued)

FOREIGN PATENT DOCUMENTS

CN  1207889 A  2/1999
CN  1298688 A  6/2001

OTHER PUBLICATIONS

Office Action mailed Apr. 27, 2011 for U.S. Appl. No. 12/198,569, filed Aug. 26, 2008, 16 pages.
(Continued)

*Primary Examiner* — Long V Le
*Assistant Examiner* — Angela M Hoffa
(74) *Attorney, Agent, or Firm* — Kory D. Christensen; Stoel Rives LLP (57) ABSTRACT

A method and apparatus are disclosed for automatic optimization of Doppler imaging parameters. The method includes obtaining and storing at least two characteristic spectral lines at a predetermined pulse repetition frequency. The method further includes optimizing at least one of the Doppler imaging parameters based on the stored at least two characteristic spectral lines and a predetermined mean noise power. In one embodiment, the characteristic spectral lines are obtained by collecting in real time the Doppler spectral lines generated at the predetermined pulse repetition frequency within a predetermined time period, and processing the collected Doppler spectral lines in real time without storing them.

19 Claims, 4 Drawing Sheets

(56) References Cited

U.S. PATENT DOCUMENTS

| | | |
|---|---|---|
| 6,577,967 B2 | 6/2003 | Mo et al. |
| 6,663,566 B2 | 12/2003 | Pan et al. |
| 6,733,454 B1 | 5/2004 | Bakircioğlu et al. |
| 6,976,960 B2* | 12/2005 | Jackson .................. 600/437 |
| 8,142,361 B2* | 3/2012 | Zhang et al. ............. 600/455 |
| 8,147,412 B2* | 4/2012 | Zhang ..................... 600/455 |
| 8,162,838 B2* | 4/2012 | Zhang ..................... 600/454 |
| 8,206,302 B2* | 6/2012 | Zhang et al. ............. 600/453 |
| 8,366,624 B1* | 2/2013 | Tamura .................... 600/455 |
| 8,435,182 B1* | 5/2013 | Tamura .................... 600/454 |
| 2008/0161691 A1* | 7/2008 | Zhang et al. ............. 600/453 |
| 2008/0242994 A1* | 10/2008 | Tamura .................... 600/453 |

OTHER PUBLICATIONS

Office Action mailed Oct. 27, 2011 for U.S. Appl. No. 12/198,569, filed Aug. 26, 2008, 14 pages.

Notice of Allowance mailed Feb. 16, 2012 for U.S. Appl. No. 12/198,569, filed Aug. 26, 2008, 12 pages.

* cited by examiner

METHOD AND APPARATUS FOR AUTOMATIC OPTIMIZATION OF DOPPLER IMAGING PARAMETERS

CROSS-REFERENCE TO RELATED APPLICATIONS

The present application claims priority to Chinese Patent Application No. 200710148460.9, entitled "Method and Apparatus for Automatic Optimization of Doppler Imaging Parameters," filed on Aug. 28, 2007, which is incorporated herein by reference.

TECHNICAL FIELD

The present disclosure relates to ultrasound imaging, and more particularly, to a method and apparatus for automatic optimization of Doppler imaging parameters.

SUMMARY OF THE INVENTION

One aspect of the present disclosure is a method for automatic optimization of Doppler imaging parameters including at least one of a pulse repetition frequency and a baseline. The method may include obtaining and storing at least two characteristic spectral lines at a predetermined pulse repetition frequency. The method may also include optimizing at least one of the Doppler imaging parameters based on the at least two stored characteristic spectral lines and a predetermined mean noise power. According to one embodiment, the at least two characteristic spectral lines are obtained by collecting in real time the Doppler spectral lines generated at the predetermined pulse repetition frequency within a predetermined time period and processing the collected Doppler spectral lines in real time without storing them.

Another aspect of the present disclosure is an apparatus for automatic optimization of Doppler imaging parameters including at least one of a pulse repetition frequency and a baseline. The apparatus may include modules for obtaining and storing at least two characteristic spectral lines at a predetermined pulse repetition frequency. The apparatus may further include a module for optimizing at least one of the Doppler imaging parameters based on the at least two stored characteristic spectral lines and a predetermined mean noise power.

DETAILED DESCRIPTION OF PREFERRED EMBODIMENTS

Pulsed Wave (PW) Doppler technology is widely used for the lossless detection and measurement of blood flow in a human body, by which one may observe the blood flow characteristics of a particular area in a human body and obtain information about blood flow velocity and distribution.

Figure 1:
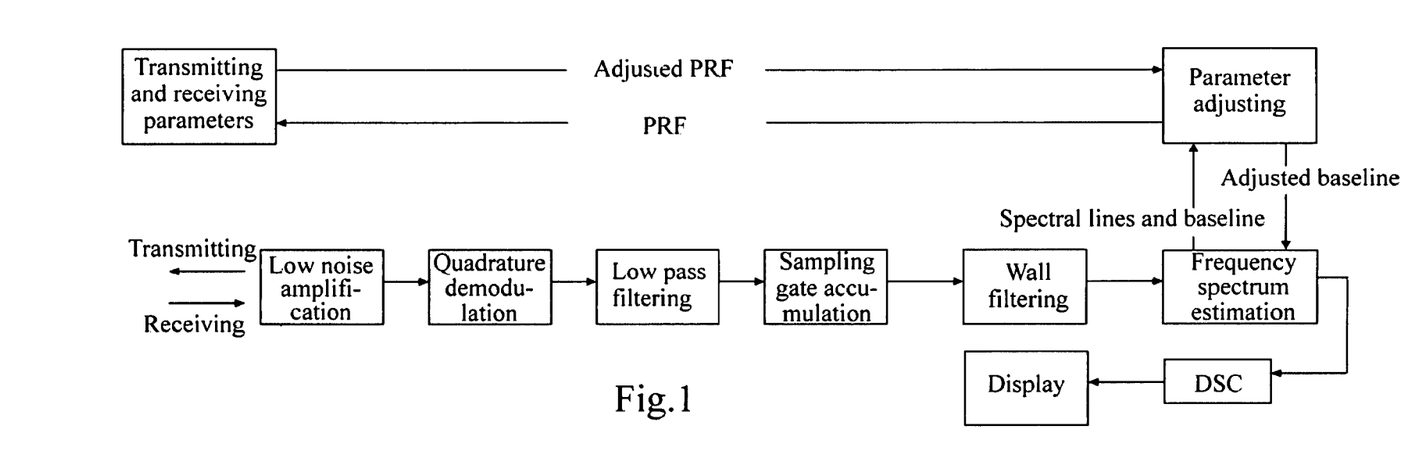
FIG. 1 is a block diagram of a typical system for optimization of Doppler imaging parameters.

FIG. 1 is a block diagram of a typical system for optimization of Doppler imaging parameters. At the beginning of the PW measurement, an operator generally places a sampling gate at a position in a two-dimensional ultrasound image of the patient to be measured. An ultrasound signal is then transmitted to the scanning position where the sampling gate is located. Scattering will occur when ultrasound signals directed into a human body encounter body cells. The signals will then reach a receiving transducer, which converts sound signals into electrical signals. The electrical signals are subjected to low-noise amplification, quadrature demodulation, and low-pass filtering to obtain two quadrature signals, i.e., in-phase (I) and quadrature (Q) signals. A sampling gate accumulation is performed for each of the quadrature signals at the sampling gate position so as to obtain a complex-valued sampling point of the Doppler signal at the current time instant.

Repeating the above-mentioned transmitting and receiving processes at a certain frequency, i.e., a Pulse Repetition Frequency (PRF), will obtain Doppler signals that vary with time. The resultant Doppler signals are wall-filtered to remove echo signals from tissues and vessel walls that have rather low frequencies. In a given time period, the filtered Doppler signals in the sampling gate are fast-Fourier-transformed to obtain a power spectrum estimation of Doppler signals, thereby obtaining, based on the Doppler effect, the distribution of the blood flow velocity in the sampling gate. Thus, the power spectrum that is varied with time forms a Doppler spectrogram.

Figure 2:
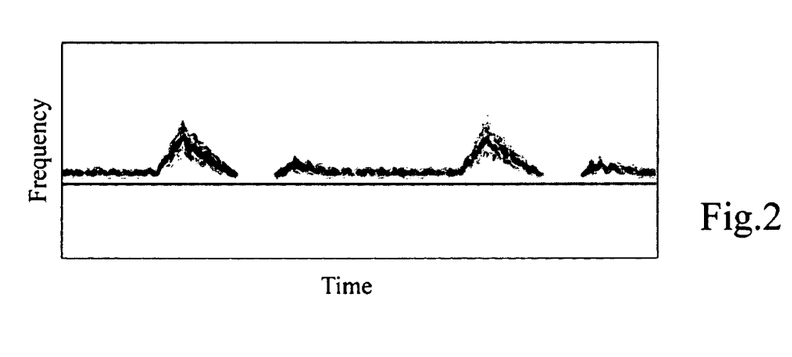
FIG. 2 is a Doppler spectrogram of carotid artery blood flow in a human body.

FIG. 2 shows a Doppler spectrogram of carotid artery blood flow in a human body. The abscissa represents time, and the ordinate represents frequency (flow velocity). Upon Digital Scanning Conversion (DSC), the Doppler spectrogram is displayed. As shown in FIG. 1, if Doppler imaging parameters need to be optimized, a parameter adjusting unit is triggered. The parameter adjusting unit first obtains a Doppler spectrogram (including Doppler spectral lines) for a certain time period, which is analyzed to obtain the adjusted pulse repetition frequency and the adjusted baseline that will, in turn, be fed back to a transceiver unit and a spectrum analyzing unit, respectively.

When the pulse repetition frequency is lower than the Nyquist frequency of the Doppler blood flow signal, or when the baseline position of the Doppler spectrogram is improperly set, the Doppler spectrogram will be aliased. In that case, the Doppler spectrogram will be wrapped around in the velocity (frequency) scale direction such that the positive velocity values may appear negative and vice versa. If the total bandwidth of the Doppler spectrum is smaller than the pulse repetition frequency, a simple baseline shift will remove the aliasing (the aliasing in this case referred to as a single-aliasing). However, if the bandwidth of the Doppler spectrum is greater than the pulse repetition frequency, the Doppler spectrogram may not be effectively unwrapped by shifting the baseline (the aliasing in this case referred to as a multi-aliasing). Instead, it is necessary to increase the pulse repetition frequency to expand the velocity scale.

A conventional Doppler ultrasound diagnostic instrument generally includes, on the operational panel, two toggle switches for adjusting the pulse repetition frequency and shifting the baseline. The switch is toggled to either increase or decrease the pulse repetition frequency or baseline by a certain amount to reach the next level preset in the system. Though exhibiting good stability, such an operation is rather time-consuming, especially when the difference between the current level and the target level is relative large, because the operator is required to manually toggle the switch for multiple times to reach the desired parameter value.

Techniques for automatically optimizing the pulse repetition frequency and the baseline realize the adjustment by processing the Doppler spectrogram for a certain time period to automatically determine the amplitude and position of the Doppler spectrogram.

U.S. Pat. No. 6,577,967 discloses one such technique, in which a Doppler spectrogram is first collected in a given time period (including at least one cardiac cycle), and then stored. To precisely determine the boundaries of the signal in the Doppler spectrogram, a noise model is provided that uses a mean noise power of a system. The mean noise power of the system is obtained by a summation of the estimated noise of various portions of the system (including the preamplifier, AD quantization noise, etc.) at different gains. A noise threshold value is estimated based on the mean noise power of the system via the noise model. Thereafter, the Doppler spectrogram, which was collected in the given time period, is processed on a per-row basis, and the boundaries of the signal may be determined based on the processing characteristics. Finally, parameters such as the pulse repetition frequency and the baseline etc. are adjusted on the basis of the boundaries as determined.

As will be understood by a person of skill in the art, the disclosed technique obtains the mean noise power by adding together the noise of various portions, which is rather complicated. Moreover, a great deal of computations and storage are required for storing all of the Doppler spectral lines in at least one cardiac cycle and processing these Doppler spectral lines on a per-row basis.

U.S. Pat. No. 6,663,566 discloses another technique, in which a Doppler spectrogram is first obtained in a given time period (including at least one cardiac cycle). All of the Doppler spectral lines for this time period are averaged in each frequency bin, and a mean power spectral line is finally obtained. The minimum value of this mean power spectral line is then searched for. A determination is then made as to whether this minimum value is a blood flow signal by utilizing characteristics such as the variance and the mean value. If it is a blood flow signal, it indicates that the blood flow signal has spanned the entire frequency axis. In this case, parameter optimization will not be performed until the pulse repetition frequency is increased. Otherwise, it indicates that noise data are contained on the frequency axis, namely, the blood flow signal has not spanned the entire frequency axis yet.

In this case, a noise threshold value is determined based on the minimum value of the mean power spectral line. With this noise threshold value, boundaries of the signal can be searched for in the mean power spectral line. The mean power spectral line is subsequently divided into a signal region and a noise region according to the signal boundaries, and a new noise threshold value is generated therefrom. A Doppler spectral line with the largest intensity at the positive boundary of the signal of the mean power spectral line is then determined from all of the Doppler spectral lines in one cardiac cycle, and a boundary of that Doppler spectral line is determined based on the new noise threshold value, the boundary being the positive boundary of the signal in the above-mentioned one cardiac cycle.

Similarly, the negative boundary of the signal in one cardiac cycle may be found out using the same procedure. With the positive and negative boundaries of the signals in one cardiac cycle determined, parameters will be capable of being automatically optimized.

The technique described in U.S. Pat. No. 6,663,566 precisely finds positive and negative boundaries of the signal in one cardiac cycle by adopting different procedures, which exhibits excellent stability. However, due to the heavy burden on computations and the great storage demand, the method, as taught, is also not suitable for operating on equipment with limited resources (e.g., an embedded chip).

The method for automatic optimization of parameters described in U.S. Pat. No. 6,447,455 is primarily directed to parameters in the case of single-aliasing. In particular, Doppler spectral lines are collected in a given time period, and energies on the positive and negative frequency axes of each of the Doppler spectral lines are summed up, and compared with one another. The larger one is considered as the direction of the Doppler spectrum. If the direction of the Doppler spectrum is positive, searching is made from the baseline upward. If the value of a frequency bin is larger than the threshold value, the peak index is updated; otherwise, it is not updated until the maximum value of the positive frequencies is reached.

Subsequently, the search turns to the maximum value of the negative frequencies and continues searching while updating the peak index until it returns to the baseline position. If the final peak index is also positive, namely, in the same direction as the Doppler spectrum, it is considered that no single-aliasing occurs. On the contrary, a single-aliasing is considered to have occurred. If the direction of the Doppler spectrum is negative, the searching is made from the baseline downward using the same steps as described above. If the final peak index is also negative, no single-aliasing occurs; otherwise, a single-aliasing occurs. If a single-aliasing occurs, it is required to increase the pulse repetition frequency.

Although the method described in the U.S. Pat. No. 6,447,455 is simple in theory, its algorithm tends to be compromised by noise interference. For example, when a speckle-like interfering signal affects the Doppler spectral line, a misjudgment will occur. In addition, in the case where the Doppler spectrum is present above and below the baseline, the algorithm is not reliable.

U.S. Patent Application No. 2007016073 introduces a method of determining whether a multi-aliasing occurs in the Doppler spectrogram by matching templates. Given a great number of Doppler spectrogram templates, the algorithm as taught ensures a high accuracy. However, because of the multiplicity of Doppler spectrogram forms, it is required to collect an unduly large number of Doppler spectrogram templates. In addition, for some special Doppler spectrograms that do not exist in the template base, the effect of the template matching is subjected to uncertainty.

Accordingly, there is a need for a method and apparatus for automatic optimization of Doppler imaging parameters, which has low requirements on system resources and exhibits excellent stability.

In order to reduce computational complexity and improve operability and stability, the present disclosure provides an improved method for automatic optimization of Doppler imaging parameters including at least one of a pulse repetition frequency and a baseline. In brief summary, the method may include obtaining and storing at least two characteristic spectral lines at a predetermined pulse repetition frequency. The method may further include optimizing at least one of the Doppler imaging parameters based on the at least two stored characteristic spectral lines and a predetermined mean noise power. In one embodiment, the at least two characteristic spectral lines are obtained by collecting in real time the Doppler spectral lines generated at the predetermined pulse repetition frequency within a predetermined time period and processing the collected Doppler spectral lines in real time without storing them.

In one embodiment, the predetermined pulse repetition frequency is selected from one of the system-allowable maximum pulse repetition frequency, the maximum pulse repetition frequency at a current detection depth, or the maximum pulse repetition frequency under a current examination mode.

In one embodiment, the at least two characteristic spectral lines include a maximum power spectral line and a mean power spectral line.

According to the present disclosure, obtaining at least two characteristic spectral lines may include: collecting in real time the Doppler spectral lines generated at the predetermined pulse repetition frequency; obtaining a final maximum power spectral line by selecting a larger power value in each frequency bin between the currently stored maximum power spectral line and the currently collected Doppler spectral line within the predetermined time period; obtaining a total power spectral line by accumulating in real time a power value in each frequency bin of the Doppler spectral lines collected in real time within the predetermined time period; and obtaining the mean power spectral line by dividing the total power spectral line by the number of the Doppler spectral lines collected in real time within the predetermined time period.

According to the present disclosure, optimizing at least one of the Doppler imaging parameters may include: filtering out the power values of the maximum power spectral line and the mean power spectral line within the frequency cutoff range of wall filtering, thereby obtaining a new maximum power spectral line and a new mean power spectral line; determining the frequency bin corresponding to the minimum power value of the new maximum power spectral line; deciding whether or not a multi-aliasing occurs by comparing the power value of the new mean power spectral line corresponding to the determined frequency bin with a first threshold value, wherein if the power value of the new mean power spectral line corresponding to the determined frequency bin is larger than the first threshold value, it is determined that the multi-aliasing occurs; otherwise, no multi-aliasing occurs; searching for boundaries of a blood flow signal based on the new maximum power spectral line and the predetermined mean noise power if no multi-aliasing occurs, the boundaries of the blood flow signal including a positive frequency boundary and a negative frequency boundary; adjusting the pulse repetition frequency down to the minimum value and the baseline to the center of a display area if no boundaries of the blood flow signal are found; and adjusting at least one of the Doppler imaging parameters based on the boundaries of the blood flow signal if the boundaries of the blood flow signal are found.

In one embodiment, the first threshold value depends on the predetermined mean noise power.

According to the present disclosure, searching for boundaries of a blood flow signal includes: searching for a negative frequency boundary of the blood flow signal in the new maximum power spectral line, which further comprises: searching from the determined frequency bin in a positive frequency direction; if the maximum power values in a number of consecutive frequency bins are larger than a second threshold value, determining that the negative frequency boundary of the blood flow signal is found; and, if not, continuing searching in the positive frequency direction until the maximum frequency bin and then searching from the minimum frequency bin up to the determined frequency bin. Searching for boundaries of a blood flow signal further comprises: searching for a positive frequency boundary of the blood flow signal in the new maximum power spectral line, which further comprises: searching from the determined frequency bin in a negative frequency direction; if the maximum power values in a number of consecutive frequency bins are larger than the second threshold value, determining that the positive frequency boundary of the blood flow signal is found; and, if not, continuing searching in the negative frequency direction until the minimum frequency bin and then searching from the maximum frequency bin down to the determined frequency bin.

In one embodiment, the second threshold value depends on the predetermined mean noise power.

In one embodiment, adjusting at least one of the Doppler imaging parameters based on the boundaries of the blood flow signal comprises adjusting the pulse repetition frequency and the baseline based on the following equations:

$$PRF_{new} = PRF_{old} \bigg/ \left( \frac{k*N}{N-(f_- - f_+)} \right) = PRF_{old}/L \qquad \text{Eq. 1}$$

$$baseline_{new} = \frac{1-k}{2}*N + (baseline_{old} - f_-)*L \qquad \text{Eq. 2}$$

where, and $PRF_{old}$ and $PRF_{new}$ are the pulse repetition frequency and the corresponding adjusted pulse repetition frequency, respectively; $baseline_{old}$ and $baseline_{new}$ are the baseline and the corresponding adjusted baseline, respectively; N is the number of frequency bins of the Doppler spectral lines; k is a predefined constant between 0 and 1, indicating the desired ratio of the frequency range of the blood flow signal to the entire frequency space; $f_-$ is the negative frequency boundary of the blood flow signal; $f_+$ is the positive frequency boundary of the blood flow signal; and L is the ratio of the pulse repetition frequency to the corresponding adjusted pulse repetition frequency.

In one embodiment, the predetermined time period is equal to at least one cardiac cycle.

In one embodiment, the predetermined mean noise power is measured in advance at different detection depths under different sampling gate width conditions.

The present disclosure also provides an apparatus for automatic optimization of Doppler imaging parameters including at least one of a pulse repetition frequency and a baseline. The apparatus may include: an obtaining module for obtaining at least two characteristic spectral lines at a predetermined pulse repetition frequency; a storage module for storing the at least two characteristic spectral lines; and an optimizing module for optimizing at least one of the Doppler imaging parameters based on the stored at least two characteristic spectral lines and a predetermined mean noise power, wherein the obtaining module obtains at least two characteristic spectral lines by collecting in real time the Doppler spectral lines generated at the predetermined pulse repetition frequency within a predetermined time period, and processing the collected Doppler spectral lines in real time without storing them.

In one embodiment, the predetermined pulse repetition frequency is selected from one of the system-allowable maximum pulse repetition frequency, the maximum pulse repetition frequency at a current detection depth, or the maximum pulse repetition frequency under a current examination mode.

In one embodiment, the at least two characteristic spectral lines include a maximum power spectral line and a mean power spectral line.

According to the present disclosure, the obtaining module may include: a collecting module for collecting in real time the Doppler spectral lines generated at the predetermined pulse repetition frequency; a maximum power spectral line obtaining module for obtaining a final maximum power spectral line by selecting a larger power value in each frequency bin between the currently stored maximum power spectral line and the currently collected Doppler spectral line within the predetermined time period; a total power spectral line obtaining module for obtaining a total power spectral line by accumulating in real time a power value in each frequency bin of the Doppler spectral lines collected in real time within the predetermined time period; and a mean power spectral line obtaining module for obtaining the mean power spectral line by dividing the total power spectral line by the number of the Doppler spectral lines collected in real time within the predetermined time period.

According to the present disclosure, the optimizing module may include: a filtering-out module for filtering out the power values of the maximum power spectral line and the mean power spectral line within the frequency cutoff range of wall filtering, thereby obtaining a new maximum power spectral line and a new mean power spectral line; a determining module for determining the frequency bin corresponding to the minimum power value of the new maximum power spectral line; an aliasing deciding module for deciding whether or not a multi-aliasing occurs by comparing the power value of the new mean power spectral line corresponding to the determined frequency bin with a first threshold value, wherein if the power value of the new mean power spectral line corresponding to the determined frequency bin is larger than the first threshold value, it is determined that the multi-aliasing occurs; otherwise, no multi-aliasing occurs; a boundary searching module for searching for boundaries of a blood flow signal based on the new maximum power spectral line and the predetermined mean noise power if no multi-aliasing occurs, the boundaries of the blood flow signal including a positive frequency boundary and a negative frequency boundary; and an adjusting module for adjusting the pulse repetition frequency down to the minimum value and the baseline to the center of a display area if no boundaries of the blood flow signal are found and adjusting at least one of the Doppler imaging parameters based on the boundaries of the blood flow signal if the boundaries of the blood flow signal are found.

In one embodiment, the first threshold value depends on the predetermined mean noise power.

In one embodiment, the predetermined time period is equal to at least one cardiac cycle.

In one embodiment, the predetermined mean noise power is measured in advance at different detection depths under different sampling gate width conditions.

It is generally required in conventional systems to store all of the Doppler spectral lines generated within a time period (including at least one cardiac cycle), which places a heavy burden on the memory. In addition, it is also generally required in conventional systems to analyze the stored Doppler spectral lines, thus involving a large number of computations. Therefore, optimizing Doppler imaging imposes high requirements on system resources in conventional systems. In contrast to the prior art, a method and apparatus according to the present disclosure may implement the automatic optimization of Doppler imaging parameters by storing and processing two characteristic spectral lines and a predetermined mean noise power, thereby requiring less resources and exhibiting low complexity and good stability.

Figure 3:
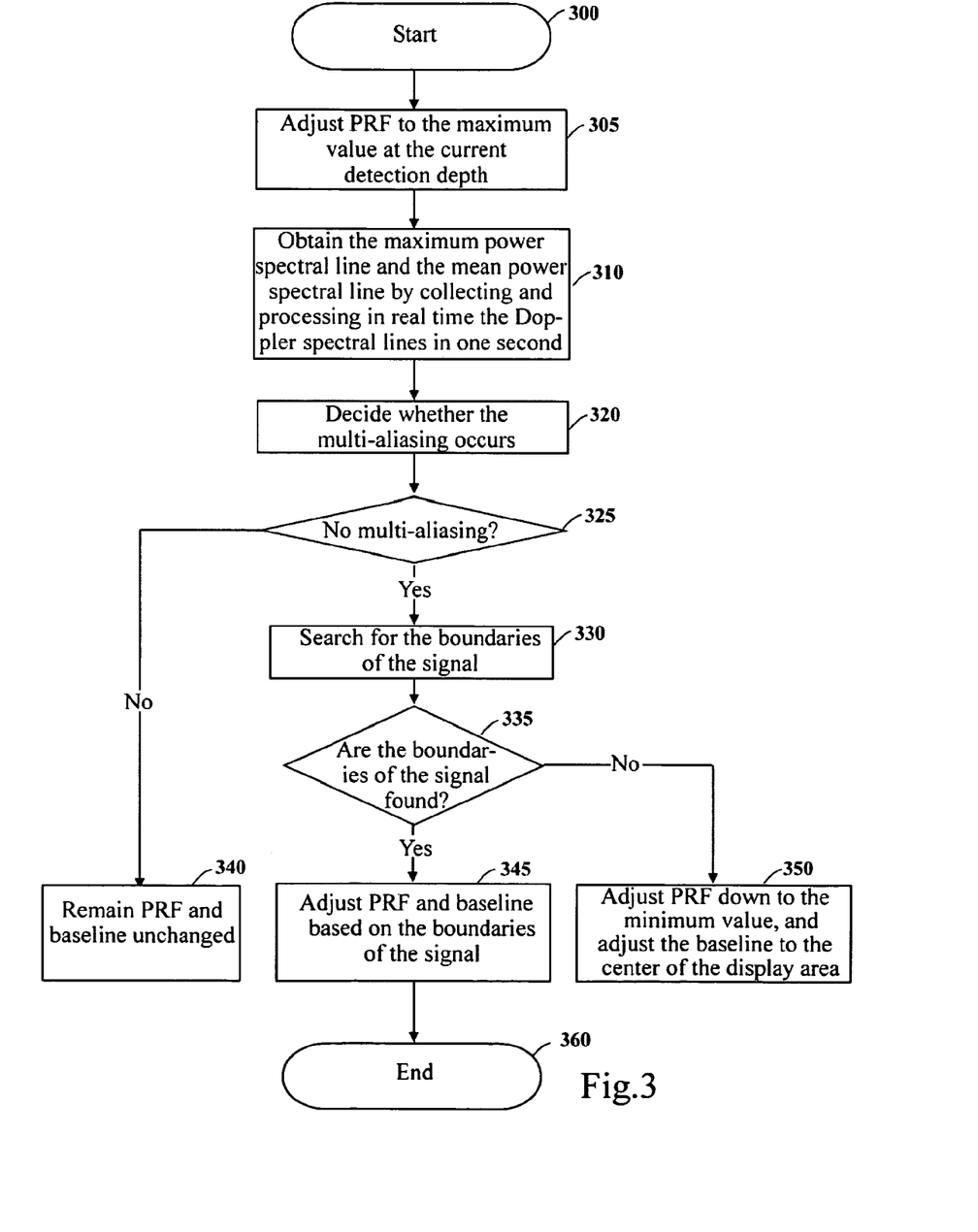
FIG. 3 is a flow diagram illustrating a method for automatic optimization of Doppler imaging parameters according to the present disclosure.

Referring now to FIG. 3, there is shown a flowchart of a method for automatic optimization of Doppler imaging parameters according to one embodiment of the disclosure. The method starts at step 300 and ends at step 360. To eliminate the multi-aliasing as much as possible, at step 305, the pulse repetition frequency is set to the maximum pulse repetition frequency at a current detection depth, which is then provided to an ultrasound transmitting unit. Assuming d is the current detection depth, and c is the speed at which the ultrasound wave propagates in a human body, the maximum pulse repetition frequency at the current detection depth may be defined as:

$$PRF_{max} = \frac{c}{2*d} \qquad \text{Eq. 3}$$

With the pulse repetition frequency set to $PRF_{max}$, because the range of blood flow velocity (blood flow Doppler frequency) becomes wider, and, in most cases, the multi-aliasing that occurs in the Doppler spectrogram can be eliminated. Unfortunately, when the blood flow passes through the position to be detected at a rather high velocity, the multi-aliasing may still exist.

The pulse repetition frequency may also be set to the system-allowable maximum pulse repetition frequency. The system-allowable maximum pulse repetition frequency at the current detection depth may exceed $PRF_{max}$. If that occurs, the system may be switched to a high pulse repetition frequency (HPRF) operation mode. Moreover, the pulse repetition frequency may also be set based on the examination mode. For example, in the mode adaptable for examination of a small organ, since the blood flow flows at a low velocity, the pulse repetition frequency may thus be set to a relatively small value.

At step 310, Doppler spectral lines generated by a frequency spectrum estimating unit within one second (assuming that the heart rate of a person is generally larger than 60 beats/min, one second is longer than one cardiac cycle) are collected and processed in real time to obtain two characteristic spectral lines, i.e. the maximum power spectral line and the mean power spectral line. The number of Doppler spectral lines generated within one second is dependent on the spectrum update rate, which may be adjusted by a user via a button on the front panel of the system. Assuming that the spectrum is updated at a rate of SpecSpeed ms, the number of the Doppler spectral lines generated within one second may be:

$$M = \frac{1000}{SpecSpeed} \qquad \text{Eq. 4}$$

Each spectral line has N frequency bins numbered as 0 to N−1 from bottom to top, each representing a different blood flow velocity. N corresponds to the number of Fast Fourier Transform (FFT) points.

The maximum power spectral line may be generated as follows. The power value in a certain frequency bin of the Doppler spectral line generated at the current time instant is compared with the power value in the corresponding frequency bin of the stored maximum power spectral line and the larger power value is used as the new power value in the corresponding frequency bin of the maximum power spectral line. The same operations are performed for each frequency bin to obtain the maximum power spectral line at the current time instant, which is then stored in the memory. Each of the Doppler spectral lines generated within one second may be processed in the same way, thereby obtaining the final maximum power spectral line, indicated by MX. In one embodiment, the initial power value in each frequency bin of the maximum power spectral line is always 0.

The mean power spectral line may be generated as follows. Add the power value in a certain frequency bin of the Doppler spectral line generated at the current time instant to the power value in the corresponding frequency bin of the stored total power spectral line and the resultant sum is used as the new power value in the corresponding frequency bin of the total power spectral line. The same operations are performed for each frequency bin to obtain the total power spectral line at the current time instant, which is then stored in the memory. Each of the Doppler spectral lines generated within one second may be processed in the same way, thereby obtaining the final total power spectral line. The total power spectral line is divided by the number of the Doppler spectral lines generated within one second to obtain the mean power spectral line, indicated by MN. In one embodiment, the initial power value in each frequency bin of the total power spectral line is always 0.

The maximum power spectral line and the mean power spectral line have been obtained as described above. All of the subsequent operations will be performed on these two characteristic spectral lines. To reduce the effect of the low-frequency, high-intensity power values caused by echoes from vessel walls and tissues on the optimization of Doppler imaging parameters, according to the setting of the cutoff frequency of wall filtering, the power values within the frequency cutoff range of wall filtering, which will be ignored in the subsequent processing, are set invalid in the maximum power spectral line and the mean power spectral line.

At step 320, a decision is made as to whether or not a multi-aliasing occurs in the Doppler spectrogram. At first, in order to search for the frequency bin corresponding to the minimum power value of the maximum power spectral line MX, referred to herein as "the minimum power frequency bin," the initial value of the minimum power frequency bin is set to 0, and then the initial minimum power value is set to the power value in the frequency bin numbered as 0 of the maximum power spectral line. Thereafter, beginning with the frequency bin numbered as 1, the power value in each of the frequency bins of the maximum power spectral line is in turn compared with the current minimum power value until the frequency bin numbered as N−1, the smaller one being used as the new minimum power value, and the corresponding frequency bin as the new minimum power frequency bin. The final minimum power frequency bin is regarded as the minimum power frequency bin of the maximum power spectral line, indicated by $f_{min}$. Next, it is decided whether the following equation is true or false:

$$MN_{fmin} < C1 \qquad \text{Eq. 5}$$

Where $MN_{fmin}$ refers to the value of the mean power spectral line MN at $f_{min}$, and C1 refers to a threshold value that is set based on a predetermined mean noise power. C1 may be, for example, two times the predetermined mean noise power. The predetermined mean noise power may be obtained by measuring the mean power of the Doppler spectrogram while the probe is idle. If Eq. 5 is false, namely, the power of the mean power spectral line at $f_{min}$ is larger than C1, the signal is considered to present at $f_{min}$. That is, the signal has spanned the entire frequency axis of the Doppler spectrogram, in which the multi-aliasing occurs. On the contrary, if Eq. 5 is true, namely, the power of the mean power spectral line at $f_{min}$ is smaller than C1, the noise is considered to present at $f_{min}$. That is, the signal has not spanned the entire frequency axis of the Doppler spectrogram, in which no multi-aliasing occurs.

At step 325, if a multi-aliasing occurs in the Doppler spectrogram, the method according to the present disclosure proceeds to step 340. At this step, the original pulse repetition frequency and the baseline remain unchanged, because the pulse repetition frequency at the moment is already the maximum pulse repetition frequency at the current detection depth. It is impossible to remove the multi-aliasing by increasing the pulse repetition frequency.

If there is no occurrence of the multi-aliasing in the Doppler spectrogram, the method proceeds to step 330. At this step, boundaries of the blood flow signal are searched for in the maximum power spectral line, wherein the boundaries of the blood flow signal includes a positive frequency boundary and a negative frequency boundary. This will be described hereafter in greater detail.

At first, a new noise threshold value C2 is determined based on the predetermined mean noise power. Then, the negative frequency boundary of the blood flow signal is searched for in the maximum power spectral line MX. C2 may be, for example, 10 times the predetermined mean noise power.

Figure 4:
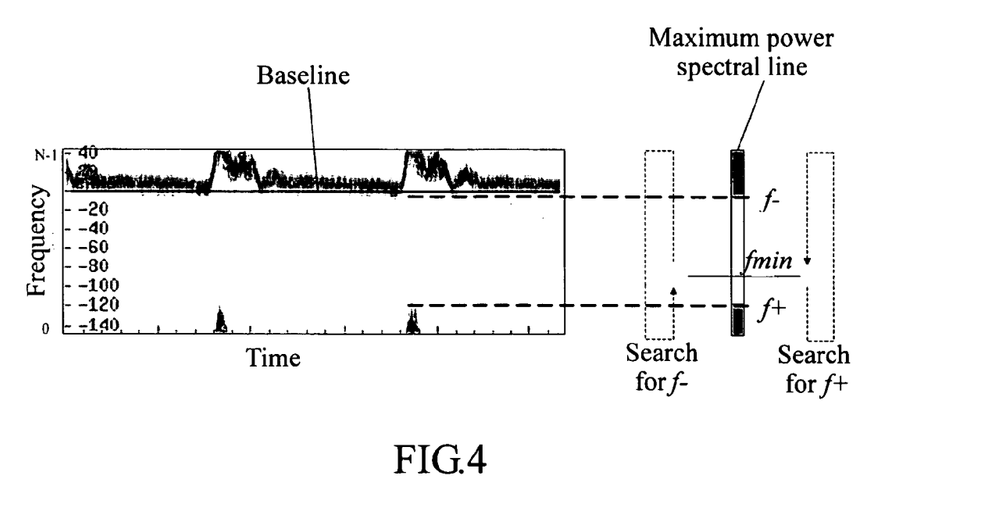
FIG. 4 is a schematic diagram illustrating how to search for boundaries of a blood flow signal in the maximum power spectral line.

FIG. 4 shows a schematic diagram illustrating how to search for the boundaries of the blood flow signal in the maximum power spectral line. In the maximum power spectral line MX, the searching starts from $f_{min}$ upward. If the maximum power values in consecutive C3 frequency bins are larger than the above new noise threshold value C2, the negative frequency boundary $f_−$ of the blood flow signal is considered to be found. Otherwise, the searching continues upward until the frequency bin numbered as N−1. Thereafter, the searching is carried on from the frequency bin numbered as 0 up to $f_{min}$.

The approach for searching for the positive frequency boundary is similar to that for searching for the negative frequency boundary, except that the searching starts from $f_{min}$ downward. After the searching reaches the frequency bin numbered as 0, it continues from the frequency bin numbered as N−1 down to $f_{min}$. The positive frequency boundary of the blood flow signal is indicated as $f_+$. C3 represents the discernable minimum frequency range of the signal. The smaller C3 is, the smaller the discernable frequency range of the signal is and the higher the sensitivity is. In one embodiment, the value of C3 should be determined in accordance with circumstances to achieve a balance between the sensitivity and the robustness of the algorithm. For example, in this embodiment, the value of C3 is 10. In practical applications, C3 may be a positive integer less than N, as required.

Returning to FIG. 3, if no boundaries of the blood flow signal can be found at step 335, the frequency range of the blood flow signal in the Doppler spectrogram is too small. The display range of the flow velocity is therefore decreased in order to correctly display the blood flow signal. Hence, the method goes to step 350, where the pulse repetition frequency is adjusted down to the minimum value in the current detection mode, and the baseline is adjusted to the center of the display area.

If the boundaries of the blood flow signal are found at step 335, the method goes to step 345, where the pulse repetition frequency and the baseline are adjusted based on the positions of $f_+$ and $f_−$. This will be descried in details below.

The process for adjusting the pulse repetition frequency is described as follows. At first, the region where the blood flow signal is distributed is delimited in the spectrogram, and then a ratio of the region as delimited to the entire frequency space is calculated. Finally, a new pulse repetition frequency is calculated based on said ratio and a desired scaling ratio.

From the maximum power spectral line in the Doppler spectrogram shown in FIG. 4, it can be seen that the signal region is given by the equation $$Ros = N − (f_− − f_+) \qquad \text{Eq. 6}$$

where Ros represents the signal region, and N represents the number of the frequency bins of the Doppler spectral lines, i.e., the number of FFT points.

The ratio of the signal region to the entire frequency space is $$\frac{Ros}{N}.$$

If the desired scaling ratio is k, the new pulse repetition frequency is calculated in accordance with:

$$PRF_{new} = PRF_{old} \bigg/ \left(\frac{k*N}{Ros}\right) = PRF_{old}/L \qquad \text{Eq. 7}$$

where $PRF_{old}$ and $PRF_{new}$ are the pulse repetition frequency and the corresponding adjusted pulse repetition frequency, respectively; k is a predefined constant between 0 and 1, indicating the desired ratio of the frequency range of the blood flow signal to the entire frequency space; and L represents a ratio of the pulse repetition frequency to the corresponding adjusted pulse repetition frequency. As the pulse repetition frequency of an ultrasound system is a discrete value, the calculated $PRF_{new}$ should be matched, in one embodiment, with the pulse repetition frequency allowed by the system. The minimum value of all values that are larger than $PRF_{new}$ may be determined from the discrete pulse repetition frequency values and used as the adjusted pulse repetition frequency.

The position of the baseline may be optimized based on the positions of $f_+$ and $f_-$, as described below. With reference to FIG. 4, the position of the adjusted base line may be defined by:

$$\text{baseline}_{new} = \frac{1-k}{2}*N + (\text{baseline}_{old} - f_-)*L \qquad \text{Eq. 8}$$

where $\text{baseline}_{old}$ and $\text{baseline}_{new}$ are the baseline and the corresponding adjusted baseline, respectively. The other parameters are defined above. Likewise, the baseline position in the ultrasound system is determined based on discrete values. Therefore, the calculated $\text{baseline}_{new}$ should be compared with possible baseline values in the system one by one, in order to find out the baseline value closest to it, which is then used as the new baseline.

Figure 5:
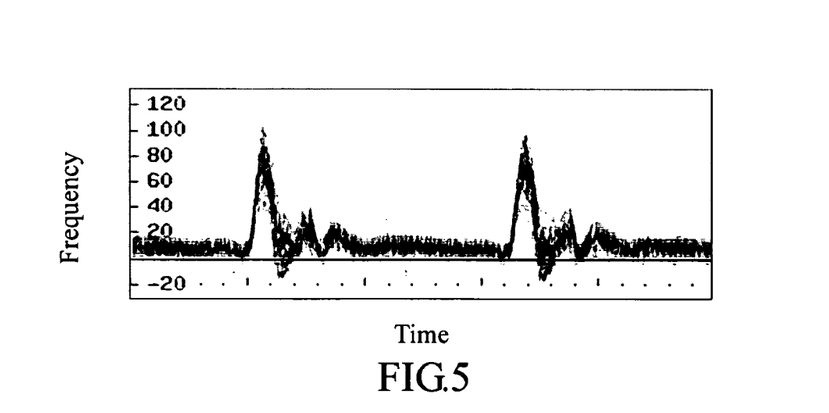
FIG. 5 is a Doppler spectrogram of FIG. 4 in which the pulse repetition frequency and the baseline has been adjusted.

Shown in FIG. 5 is the spectrogram of FIG. 4 with the pulse repetition frequency and the baseline adjusted according to the techniques of the present disclosure. It can be seen from FIG. 5 that no aliasing exists in the Doppler spectrogram with the related parameters adjusted, and that the frequency range of the signal takes up a suitable proportion of the entire frequency space.

Figure 6:
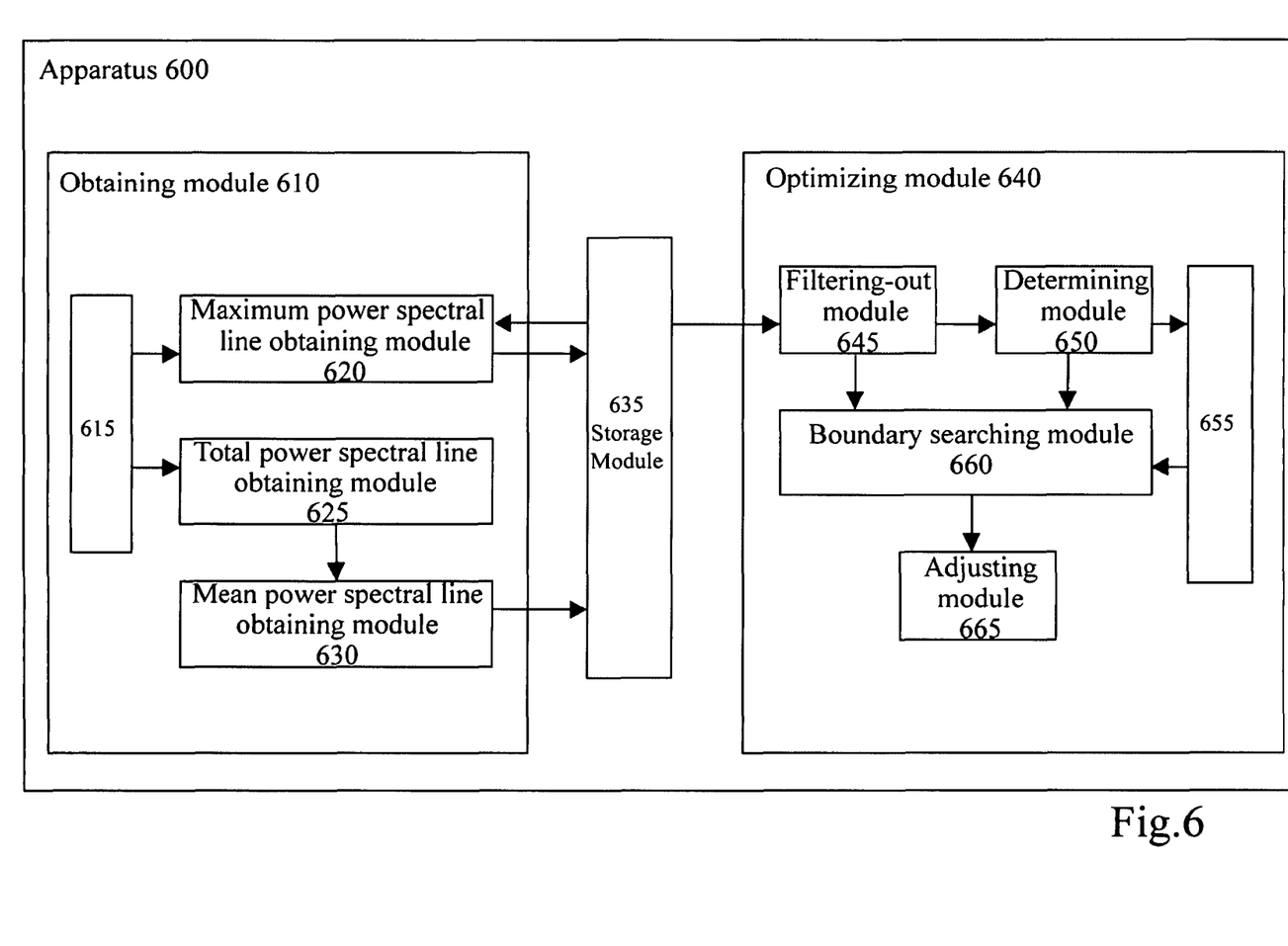
FIG. 6 is a block diagram of an apparatus for automatic optimization of Doppler imaging parameters according to the present disclosure.

FIG. 6 is a block diagram of an apparatus 600 for automatic optimization of Doppler imaging parameters according to the present disclosure. As shown in FIG. 6, the apparatus 600 comprises an obtaining module 610, a storage module 635 and an optimizing module 640. According to an embodiment of the present disclosure, to implement the automatic optimization of Doppler imaging parameters, the ultrasound transmitting unit in the ultrasound system transmits ultrasound waves according to $PRF_{max}$. The obtaining module 610 obtains a maximum power spectral line and a mean power spectral line by collecting in real time the Doppler spectral lines generated by the frequency spectrum estimating unit within one second, and processing the collected Doppler spectral lines in real time without storing them. The storage module 635 stores the maximum power spectral line and the mean power spectral line. The optimizing module 640 optimizes at least one of the Doppler imaging parameters based on the stored maximum power spectral line, the mean power spectral line, and the predetermined mean noise power. The predetermined mean noise power is measured in advance at different detection depths under different sampling gate width conditions.

According to an embodiment of the present disclosure, the obtaining module 610 comprises a collecting module 615, a maximum power spectral line obtaining module 620, a total power spectral line obtaining module 625 and a mean power spectral line obtaining module 630. The collecting module 615 collects in real time the Doppler spectral lines generated by the frequency spectrum estimating unit. The maximum power spectral line obtaining module 620 obtains a final maximum power spectral line by selecting a larger power value in each frequency bin between the currently stored maximum power spectral line and the currently collected Doppler spectral line within one second. The total power spectral line obtaining module 625 obtains a total power spectral line by accumulating in real time a power value in each frequency bin of the Doppler spectral lines collected in real time within one second, and provides the total power spectral line to the mean power spectral line obtaining module 630. The mean power spectral line obtaining module 630 obtains a mean power spectral line by dividing the total power spectral line by the number of the Doppler spectral lines collected in real time within one second.

In one embodiment, the optimizing module 640 comprises a filtering-out module 645, a determining module 650, an aliasing deciding module 655, a boundary searching module 660 and an adjusting module 665. The filtering-out module 645 filters out the power values of the stored maximum power spectral line and mean power spectral line within the frequency cutoff range of wall filtering, thereby obtaining the new maximum power spectral line and the new mean power spectral line. The determining module 650 determines the frequency bin $f_{min}$ corresponding to the minimum power value of the new maximum power spectral line. The aliasing deciding module 655 decides whether or not a multi-aliasing occurs by comparing the power value of the new mean power spectral line at $f_{min}$ with C1. If the power value of the new mean power spectral line at $f_{min}$ is larger than C1, a multi-aliasing is determined to have occurred. Otherwise, there is no occurrence of a multi-aliasing. In case there is no occurrence of a multi-aliasing, the boundary searching module 660 searches for the boundaries of the blood flow signal based on the new maximum power spectral line and the predetermined mean noise power. The adjusting module 665 adjusts the Doppler imaging parameters based on the output of the boundary searching module 660. When the boundaries of the blood flow signal can not be found, the pulse repetition frequency will be adjusted down to the minimum value, and the baseline will be adjusted to the center of the display area. On the contrary, when the boundaries of the blood flow signal are found, at least one of the Doppler imaging parameters will be adjusted based on the boundaries of the blood flow signal.

The method and apparatus according to the present disclosure has been proven feasible in the color Doppler diagnostic system, which is applicable not only to the real time optimization of Doppler imaging parameters, but also to the offline optimization of Doppler imaging parameters.

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Although the invention has been described above with reference to the specific embodiments thereof, it is not intended that the invention be limited to the above-mentioned embodiments. Various modifications and alternations may be made to the present invention without departing from the scope of the present invention. The scope of the present invention is defined by the appended claims. Such words as "first" and "second" used in the description and the claims of the present invention are merely illustrative and should by no means be considered as restrictive.

What is claimed is:

1. A method for automatic optimization of Doppler imaging parameters including at least one of a pulse repetition frequency and a baseline, the method comprising:
    obtaining at least two characteristic spectral lines at a predetermined pulse repetition frequency, wherein the at least two characteristic spectral lines include a maximum power spectral line and a mean power spectral line;
    storing the at least two characteristic spectral lines; and
    optimizing at least one of the Doppler imaging parameters based on the stored at least two characteristic spectral lines and a predetermined mean noise power,
    wherein the at least two characteristic spectral lines are obtained by collecting, as Doppler spectral lines are generated, the Doppler spectral lines generated at the predetermined pulse repetition frequency within a predetermined time period, and processing the collected Doppler spectral lines without storing the collected Doppler spectral lines.

2. The method according to claim 1, wherein the predetermined pulse repetition frequency is a system-allowable maximum pulse repetition frequency, a maximum pulse repetition frequency at a current detection depth, or a maximum pulse repetition frequency under a current examination mode.

3. The method according to claim 1, wherein obtaining the at least two characteristic spectral lines comprises:
    collecting, as the Doppler spectral lines are generated, the Doppler spectral lines generated at the predetermined pulse repetition frequency;
    obtaining a final maximum power spectral line by selecting a larger power value in each frequency bin between the stored maximum power spectral line and the collected Doppler spectral line within the predetermined time period;
    obtaining a total power spectral line by accumulating, as the Doppler spectral lines are generated, a power value in each frequency bin of the Doppler spectral lines collected as the Doppler spectral lines are generated within the predetermined time period; and
    obtaining the mean power spectral line by dividing the total power spectral line by the number of the Doppler spectral lines collected as the Doppler spectral lines are generated within the predetermined time period.

4. The method according to claim 1, wherein optimizing the at least one of the Doppler imaging parameters comprises:
    filtering out power values of the maximum power spectral line and the mean power spectral line within a frequency cutoff range of wall filtering to obtain a new maximum power spectral line and a new mean power spectral line;
    determining a frequency bin corresponding to a minimum power value of the new maximum power spectral line;
    deciding whether or not a multi-aliasing occurs by comparing a power value of the new mean power spectral line corresponding to the determined frequency bin with a first threshold value, wherein if the power value of the new mean power spectral line corresponding to the determined frequency bin is larger than the first threshold value, occurring of a multi-aliasing is determined; otherwise, no multi-aliasing occurs;
    searching for boundaries of a blood flow signal based on the new maximum power spectral line and the predetermined mean noise power if no multi-aliasing occurs, wherein the boundaries of the blood flow signal include a positive frequency boundary and a negative frequency boundary;

adjusting the pulse repetition frequency down to a minimum value and the baseline to a center of a display area if no boundaries of the blood flow signal are found; and adjusting at least one of the Doppler imaging parameters based on the boundaries of the blood flow signal if the boundaries of the blood flow signal are found.

5. The method of claim 4, wherein the first threshold value depends on the predetermined mean noise power.

6. The method of claim 4, wherein searching for the boundaries of the blood flow signal comprises:

searching for the negative frequency boundary of the blood flow signal in the new maximum power spectral line, which further comprises: searching from the determined frequency bin in a positive frequency direction; if maximum power values in a number of consecutive frequency bins are larger than a second threshold value, determining that the negative frequency boundary of the blood flow signal is found; and, if not, continuing searching in the positive frequency direction until a maximum frequency bin and then searching from a minimum frequency bin up to the determined frequency bin; and searching for the positive frequency boundary of the blood flow signal in the new maximum power spectral line, which further comprises: searching from the determined frequency bin in a negative frequency direction; if the maximum power values in a number of consecutive frequency bins are larger than the second threshold value, determining that the positive frequency boundary of the blood flow signal is found; and, if not, continuing searching in the negative frequency direction until the minimum frequency bin and then searching from the maximum frequency bin down to the determined frequency bin.

7. The method of claim 6, wherein the second threshold value depends on the predetermined mean noise power.

8. The method according to claim 4, wherein adjusting at least one of the Doppler imaging parameters based on the boundaries of the blood flow signal comprises adjusting the pulse repetition frequency and the baseline based on following equations:

$$PRF_{new} = PRF_{old} \Big/ \left( \frac{k*N}{N-(f_- - f_+)} \right) = PRF_{old}/L$$

$$baseline_{new} = \frac{1-k}{2}*N + (baseline_{old} - f_-)*L$$

where, $PRF_{old}$ and $PRF_{new}$ are the pulse repetition frequency and the corresponding adjusted pulse repetition frequency, respectively; $baseline_{old}$ and $baseline_{new}$ are the baseline and the corresponding adjusted baseline, respectively; N is the number of frequency bins of the Doppler spectral lines; k is a predefined constant between 0 and 1, indicating a desired ratio of the frequency range of the blood flow signal to a entire frequency space; $f_-$ the negative frequency boundary of the blood flow signal; $f_+$ is the positive frequency boundary of the blood flow signal; and L is a ratio of the pulse repetition frequency to the corresponding adjusted pulse repetition frequency.

9. The method according to claim 1, wherein the predetermined time period is equal to at least one cardiac cycle.

10. The method according to claim 1, wherein the predetermined mean noise power is measured in advance at different detection depths under different sampling gate width conditions.

11. An apparatus for automatic optimization of Doppler imaging parameters including at least one of a pulse repetition frequency and a baseline, the apparatus comprising:

an obtaining module configured to obtain at least two characteristic spectral lines at a predetermined pulse repetition frequency, wherein the at least two characteristic spectral lines include a maximum power spectral line and a mean power spectral line;

a storage module configured to store the at least two characteristic spectral lines; and an optimizing module configured to optimize at least one of the Doppler imaging parameters based on the stored at least two characteristic spectral lines and a predetermined mean noise power, wherein the obtaining module obtains at least two characteristic spectral lines by collecting, as Doppler spectral lines are generated, the Doppler spectral lines generated at the predetermined pulse repetition frequency within a predetermined time period, and processing the collected Doppler spectral lines without storing the collected Doppler spectral lines.

12. The apparatus according to claim 11, wherein the predetermined pulse repetition frequency is a system-allowable maximum pulse repetition frequency, a maximum pulse repetition frequency at a current detection depth, or a maximum pulse repetition frequency under a current examination mode.

13. The apparatus according to claim 11, wherein the obtaining module comprises:

a collecting module configured to collect, as the Doppler spectral lines are generated, the Doppler spectral lines generated at the predetermined pulse repetition frequency;

a maximum power spectral line obtaining module configured to obtain a final maximum power spectral line by selecting a larger power value in each frequency bin between the stored maximum power spectral line and the collected Doppler spectral line within the predetermined time period;

a total power spectral line obtaining module configured to obtain a total power spectral line by accumulating, as the Doppler spectral lines are generated, a power value in each frequency bin of the Doppler spectral lines collected as the Doppler spectral lines are generated within the predetermined time period; and a mean power spectral line obtaining module configured to obtain the mean power spectral line by dividing the total power spectral line by the number of the Doppler spectral lines collected as the Doppler spectral lines are generated within the predetermined time period.

14. The apparatus according to claim 11, wherein the optimizing module comprises:

a filtering-out module configured to filter out power values of the maximum power spectral line and the mean power spectral line within a frequency cutoff range of wall filtering to obtain a new maximum power spectral line and a new mean power spectral line;

a determining module configured to determine a frequency bin corresponding to a minimum power value of the new maximum power spectral line;

an aliasing deciding module configured to decide whether or not a multi-aliasing occurs by comparing a power value of the new mean power spectral line corresponding to the determined frequency bin with a first threshold value, wherein if the power value of the new mean power spectral line corresponding to the determined frequency bin is larger than the first threshold value, occurring of a multi-aliasing is determined; otherwise, no multi-aliasing occurs;

a boundary searching module configured to search for boundaries of a blood flow signal based on the new maximum power spectral line and the predetermined mean noise power if no multi-aliasing occurs, wherein the boundaries of the blood flow signal include a positive frequency boundary and a negative frequency boundary; and an adjusting module configured to adjust the pulse repetition frequency down to a minimum value and the baseline to a center of a display area if no boundaries of the blood flow signal are found and to adjust at least one of the Doppler imaging parameters based on the boundaries of the blood flow signal if the boundaries of the blood flow signal are found.

15. The apparatus of claim 14, wherein the first threshold value depends on the predetermined mean noise power.

16. The apparatus according to claim 11, wherein the predetermined time period is equal to at least one cardiac cycle.

17. The apparatus according to claim 11, wherein the predetermined mean noise power is measured in advance at different detection depths under different sampling gate width conditions.

18. A non-transitory computer-readable medium comprising program code for causing a computer to perform a method for automatic optimization of Doppler imaging parameters including at least one of a pulse repetition frequency and a baseline, the method comprising:

obtaining at least two characteristic spectral lines at a predetermined pulse repetition frequency, wherein the at least two characteristic spectral lines include a maximum power spectral line and a mean power spectral line;

storing the at least two characteristic spectral lines; and optimizing at least one of the Doppler imaging parameters based on the stored at least two characteristic spectral lines and a predetermined mean noise power, wherein the at least two characteristic spectral lines are obtained by collecting as Doppler spectral lines are generated, the Doppler spectral lines generated at the predetermined pulse repetition frequency within a predetermined time period, and processing the collected Doppler spectral lines without storing the collected Doppler spectral lines.

19. An apparatus for automatic optimization of Doppler imaging parameters including at least one of a pulse repetition frequency and a baseline, the apparatus comprising:

means for obtaining at least two characteristic spectral lines at a predetermined pulse repetition frequency, wherein the at least two characteristic spectral lines include a maximum power spectral line and a mean power spectral line;

means for storing the at least two characteristic spectral lines; and means for optimizing at least one of the Doppler imaging parameters based on the stored at least two characteristic spectral lines and a predetermined mean noise power, wherein the at least two characteristic spectral lines are obtained by collecting as Doppler spectral lines are generated, the Doppler spectral lines generated at the predetermined pulse repetition frequency within a predetermined time period, and processing the collected Doppler spectral lines without storing the collected Doppler spectral lines.

* * * * *